US011498052B2

(12) United States Patent
Hjortfors et al.

(10) Patent No.: US 11,498,052 B2
(45) Date of Patent: Nov. 15, 2022

(54) METHOD FOR RECYCLING SATURATED ACTIVE ADSORBENT OF A FILTER MODULE

(71) Applicant: ABSOLENT AB, Lidköping (SE)

(72) Inventors: Jan Hjortfors, Skara (SE); Anders Knutsson, Järpås (SE); Joel Svanström, Lidköping (SE); Jan Jan Berndtsson, Kvänum (SE)

(73) Assignee: ABSOLENT AB, Lidköping (SE)

( * ) Notice: Subject to any disclaimer, the term of this patent is extended or adjusted under 35 U.S.C. 154(b) by 88 days.

(21) Appl. No.: 16/651,064

(22) PCT Filed: Oct. 1, 2018

(86) PCT No.: PCT/SE2018/051001
§ 371 (c)(1),
(2) Date: Mar. 26, 2020

(87) PCT Pub. No.: WO2019/066716
PCT Pub. Date: Apr. 4, 2019

(65) Prior Publication Data
US 2020/0222878 A1 Jul. 16, 2020

(30) Foreign Application Priority Data
Oct. 1, 2017 (SE) .................................. 1730272-0

(51) Int. Cl.
*B01D 53/04* (2006.01)
*A61L 9/014* (2006.01)
*B01J 20/34* (2006.01)

(52) U.S. Cl.
CPC .......... *B01J 20/34* (2013.01); *B01D 53/0415* (2013.01); *B01D 2259/40083* (2013.01)

(58) Field of Classification Search
CPC .. A61L 9/014; A61L 2209/14; A61L 2209/22; B01D 53/0415;
(Continued)

(56) References Cited

U.S. PATENT DOCUMENTS 1,681,531 A * 8/1928 Gannon .................. A61L 9/01
96/147
2,087,157 A * 7/1937 Lind ...................... B01J 47/024
141/2
(Continued)

FOREIGN PATENT DOCUMENTS

| DE | 10354037 A1 | 6/2005 |
| EP | 0517021 A1 | 12/1992 |
| GB | 2 063 095 A | 6/1981 |

OTHER PUBLICATIONS

International Search Report dated Dec. 18, 2018, corresponding to International Application No. PCT/SE2018/051001.

*Primary Examiner* — Frank M Lawrence, Jr.
(74) *Attorney, Agent, or Firm* — Ladas & Parry LLP; Malcolm J. MacDonald

(57) ABSTRACT

A method of recycling an saturated adsorbent (3) of a filter module (1) of an industrial process plant (15), wherein a first process (17) includes removing the saturated adsorbent (3) from the filter module (1), a fourth process (20) includes washing and reactivating the saturated adsorbent, a fifth process (21) includes drying and packing the reactivated adsorbent in airtight containers, and a seventh process (23) includes replacing the saturated adsorbent by reactivated adsorbent in the filter module (1).

4 Claims, 2 Drawing Sheets

(58) Field of Classification Search
CPC . B01D 2259/40083; B01D 2259/40086; B01J 20/34; C01B 32/36
USPC ......... 96/108, 143–146; 95/90, 148; 502/20, 502/34, 56
See application file for complete search history.

(56) References Cited

U.S. PATENT DOCUMENTS

| | | | | |
|---|---|---|---|---|
| 3,240,567 | A | * | 3/1966 | Caparreli ............... A62B 19/00 206/525 |
| 3,801,514 | A | * | 4/1974 | Joseph .................... C01B 32/36 502/55 |
| 3,871,849 | A | | 3/1975 | Smith et al. |
| 3,874,427 | A | * | 4/1975 | Tiggelbeck .......... B67D 7/0476 141/52 |
| 4,957,721 | A | * | 9/1990 | Lonsinger ............... C01B 32/36 423/460 |
| 5,198,398 | A | * | 3/1993 | van Duijn ............... C01B 32/39 210/189 |
| 7,018,447 | B2 | * | 3/2006 | McAnespie ............ B01D 53/06 502/22 |
| 2013/0019749 | A1 | * | 1/2013 | Hufton ................... B01D 53/02 95/95 |
| 2016/0222302 | A1 | * | 8/2016 | Zhao .................... B01J 20/3204 |

* cited by examiner

METHOD FOR RECYCLING SATURATED ACTIVE ADSORBENT OF A FILTER MODULE

TECHNICAL FIELD

The present invention concerns gas filtering in an industrial process plant. More precisely the invention concerns adsorption of molecules in a gas stream. In particular the invention concerns a method and a system for recycling of wasted adsorbents.

BACKGROUND OF THE INVENTION

There are known great many solutions for gas particles filtration within industrial processes. This includes systems for filtering oil mist or oil smoke as well as dust. However when it comes to removing gas molecules such as odour not so many solutions are known. For filtering odour or poisonous molecules from a process gas mainly three methods are feasible; adsorption, condensing or oxidation. Condensing comprises chilling the gas into liquid phase. Oxidation comprises catalytic combustion by an open flame. Mostly an adsorbent like active carbon is used to adsorb the odour from the gas. However metal oxides like copper oxide and alumina oxide may be a more effective adsorbent than carbon for certain molecules.

Adsorption is the adhesion of atoms, ions or molecules from a gas, liquid or dissolved solid to a surface. This process creates a film of the adsorbate on the surface of the adsorbent. It differs from absorption in which a fluid is dissolved by a liquid or solid. Adsorption is a surface-based process while absorption involves the whole volume of the material. However having adsorbed a certain amount of gas molecules the adsorbent will be saturated. When saturated the adsorbent must be replaced by a fresh adsorbent. Therefore the adsorbent must be easy to replace.

Already in the design of these filters there is an obvious problem of providing a long-lasting seal between the upstream side spaces from the downstream side spaces. To be efficient all gas must pass the active adsorbent and not slip around the trays. Hence the trays must have a seal all around the trays while still being able to be removed for inspection and refill. In known filters the gas flow may not be uniform through the filter layers. Since there might be an uneven pressure profile in the upside set of spaces also the flow will be affected. Hence the activated adsorbent will be saturated at one side on the tray while the other side will still contain active adsorbent. This leads to the whole adsorbent layer having to be exchanged prematurely. Thus for creating a long lasting active adsorbent filter great care must be taken to create a gas flow such that no parts of the active adsorbent layer is saturated prior to other parts.

Saturated active adsorbent is wasted and must be replaced. Commonly the trays containing the wasted active adsorbent are sent to a refilling facility where the active adsorbent containing trays are recycled. Waste adsorbent from the dismantled trays is pored out in a pile in the back yard. Then the tray is relined and filled with new active adsorbent from a pile next to the first pile. It is known the trays being dismantled into parts where metal and tissues are sent to different locations for recirculation. This is a cumbersome and dirty work. Thus known recycling methods do not contain a full circle. Besides, the process involves a plurality of work stations. Also the plurality of transports to and from the recycling facilities does not result in an effective recycling process.

For recycling purposes the trays are built up far too complicated for an effective dismantling into recyclable parts. Except for the wasted adsorbent there is a plurality of sheets, scrims and woven textures which has to be taken care of separately. Often the wasted adsorbent is simply separated from the trays and transported for combustion. The tray and its content may often provide heavy loads. Exchanging such a tray may require more than one person or the need for a lifting aid.

A method for recycling waste active adsorbent discarded from a gas treatment is previously known. Waste active adsorbent and coal discarded from a gas treatment facility are stored in an existing coal storage plant or the like close to the combustion facility. During storage in the coal storage plant sprinkled water is discharged to the waste active adsorbent and coal via a sprinkling means. This is said to remove the chemicals adsorbed on the waste active adsorbent and the adsorbed components. Thereafter the waste active adsorbent and the coal are pulverized by a pulverizing means. The pulverized coal mixture of the waste active adsorbent and the coal is burned in a combustion facility. Low-grade coal can be used as coal.

From U.S. Pat. No. 3,871,849 a disposable carbon filter is previously known. The object of which is to prevent the deleterious effects of settling of the filter material. Accordingly the disposable carbon filter comprises at least one paperboard carton containing granular active carbon compressively contained by a porous scrim material. More specifically the carbon filter comprises at least one six-sided carton tray to be stacked in a filter assembly divided into chambers. When the carbon filter beds are spent trays may be removed through these chambers for disposal.

The flow of gas to be purified is in the longitudinal direction. Such an arrangement requires that the gas be directed through the trays at right angles to the direction at which it enters the housing. It is therefore necessary to change direction of the gas within the housing. To accomplish such a change it is required that the alternate ends of successive adsorbent filter trays be connected to fluid impervious plate means to define gas receiving and gas expelling chambers. Such chambers are arranged parallel to the direction of gas flow through the housing so that the gas flowing into the gas receiving chambers flows into one end thereof, changes direction by 90 degrees to pass through a filter tray, comprising either the top or bottom surface of the chamber, and finally changes direction back by 90 degrees to pass out of the housing through an expelling chamber.

Each of the cartons is lined with a porous scrim material and then completely filled with active granular carbon particles. A second layer of porous scrim or other fluid pervious covering is then laid over the carbon particles in compressive fashion and a precut facing of sheet material having a flow through orifice is laid thereover to form a carbon holding cavity containing the active granular carbon particles under compression. In an embodiment the carton contains a plurality of porous scrim bags containing carbon arranged side by side.

SUMMARY OF THE INVENTION

A primary object of the present invention is to seek ways to improve the recycling of wasted adsorbents of a process gas filter.

This object is achieved according to the invention by a method for recycling wasted active adsorbent as hereinafter set forth, or by a system as hereinafter set forth. Preferred embodiments are also hereinafter set forth.

According to the invention the recycling of waste active adsorbent comprises a closed circle. The active adsorbent is contained in permeable bags which are placed close to each other on a carrier in a filter module. By the expression "bag" is understood a formable enclosure with aperture at one end. A bag has no determined envelope surface. Thus a bag containing granular material can be formed to fill whatever shape of a receiving cavity. The active adsorbent filled bags are arranged close to each other to completely fill out the receiving cavity. By the flexible structure of the bags the layers of flexible bags containing active adsorbent can be assembled very tight and consequently no air will pass without coming into contact with the adsorbent. In an embodiment the flexible container comprises a sack which is a coarse weave storage device with one end opening.

In an embodiment the carrier comprises a diffuser for carrying the bags and spreading the gas stream. The bag comprises a gas permeable material yet providing a closed container for keeping the active adsorbent. By providing the active adsorbent in bags a clean environment is secured. Besides, the adsorbent bags are light weight and may be handled by a single person without the help of other equipment. Thus a person may perform an exchange of saturated active adsorbent of his own and without being polluted by adsorbent.

When the adsorbent is saturated the bags must be removed from the filter module and transported to a recycling facility. In the recycling facility the waste adsorbent is reactivated while still being contained in the bags. Immediately after reactivation the bags are enclosed in vacuum tight containers. Odour of an ambient gas or the air may otherwise start the saturation process. Then the bags containing reactivated active adsorbent are sent back to the process plant. While a first set of bags are adsorbing odour at the process plant a second set of bags are being reactivated at the recycling facility. When needed the reactivated adsorbent bags are packed and sent to the process plant and the bags containing saturated active adsorbent is sent back. This ensures a minimum of transports. In an embodiment of the invention the process plant comprises the recycling facility. In this embodiment the transport is at a minimum.

According to the invention the odour-removing filter comprises a layer of active adsorbent particles arranged perpendicular to the main gas stream. In an embodiment the layer of active adsorbent particles comprises a plurality of tissue bags containing the active adsorbent. In an embodiment the bags are arranged on a horizontal carrier in a housing receiving gas in a vertical direction. In an embodiment the carrier comprises a diffuser for spreading the gas stream. In an embodiment the bags are arranged between two vertical carriers in a housing receiving gas in a horizontal direction. By arranging the gas flow perpendicular to the active adsorbent layer the pressure profile will be even and thus also the gas flow. By encapsulating the active adsorbent in tissue bags a great variety of filter may be designed. The bags are easy and clean to handle, easy to build up the filter and easy to deposit.

In an embodiment of the invention the bags are arranged side by side in a first layer on a diffuser comprising a grid. In an embodiment a second layer is arranged on a second diffuser in the housing. In this second layer the bags are arranged in parallel with the first layer. In an embodiment the second layer is arranged in a distance to the first layer. The presence of a diffuser provides a smooth pressure profile and thus an even gas flow.

The active adsorbent containing bags are conveniently provided from a woven tissue. In an embodiment the bags are made of fabric. In an embodiment the bags comprises heat resistant material. This enables wasted adsorbent to be reactive while contained in the bags.

The housing comprises a cubic shape and is arranged to become a module in a process filter system. Thus the filter housing may be dismounted from the filter system. In a recycling system the bags containing saturated adsorbent are picked up and sent for reactivation. Fresh bags containing active or reactivated adsorbents are packed in the housing and the module is put back in the filter system. The simple design of these modules makes the change go very quickly.

In the recycling system the saturated active adsorbent bags are sent to a reactivation facility. There the waste adsorbent is reactivated while contained in the bags. The reactivation method may comprise a washing by a suitable solvent liquid, heating by steam and drying. These processes are performed while the active adsorbent is contained in the bags. After reactivation each bag is packed in an air tight container and sent back to the filter user. The container might be a vacuum tight plastic bag. This packing ensures the filter bags to be stored without the active adsorbent being partly saturated.

Due to incomplete regeneration the lifetime of the active adsorbent will be shortened by the number of reactivation. When the lifetime has been unacceptable shortened the bag will be sent for combustion. Then the recirculation of that bag is terminated. These bags will still be part of the global recycling system. Bags containing fresh active adsorbent will then be introduced in the recycling process.

In a first aspect of the invention the object is achieved by a method of recycling saturated adsorbents of a filter module of an industrial process plant, wherein saturated active adsorbents is removed from the filter module, washing and reactivating the saturated adsorbents, drying and packing the reactivated adsorbents in airtight containers, and replacing the waste adsorbents by reactivated adsorbents in the filter module. In an embodiment the method further comprises packing the wasted saturated adsorbents in a container, transporting the saturated adsorbents to a reactivation facility, and transporting the reactivated adsorbents back to the industrial process plant. In an embodiment the method further comprises providing the adsorbents to be contained in heat resistant permeable bags.

In a second aspect of the invention the object is achieved by a system for recycling an adsorbent of a filter module in an industrial process plant, the saturated adsorbents being contained in gas permeable heat resistant bags, wherein the system comprises means for packing the wasted adsorbent containing bags, transport means for sending the package to a reactivation facility, means for reactivating the saturated adsorbent while still in their bags, means for drying and packing the reactivated adsorbent bags, and transport means for sending the bags back to the process plant. In an embodiment the system further comprises means for pacing the waste saturated adsorbents and means for replacing the waste saturated adsorbents by reactivated active adsorbents.

BRIEF DESCRIPTION OF THE DRAWINGS

Other features and advantages of the present invention will become more apparent to a person skilled in the art from the following detailed description in conjunction with the appended drawings in which.

DESCRIPTION OF PREFERRED EMBODIMENTS

Figure 1:
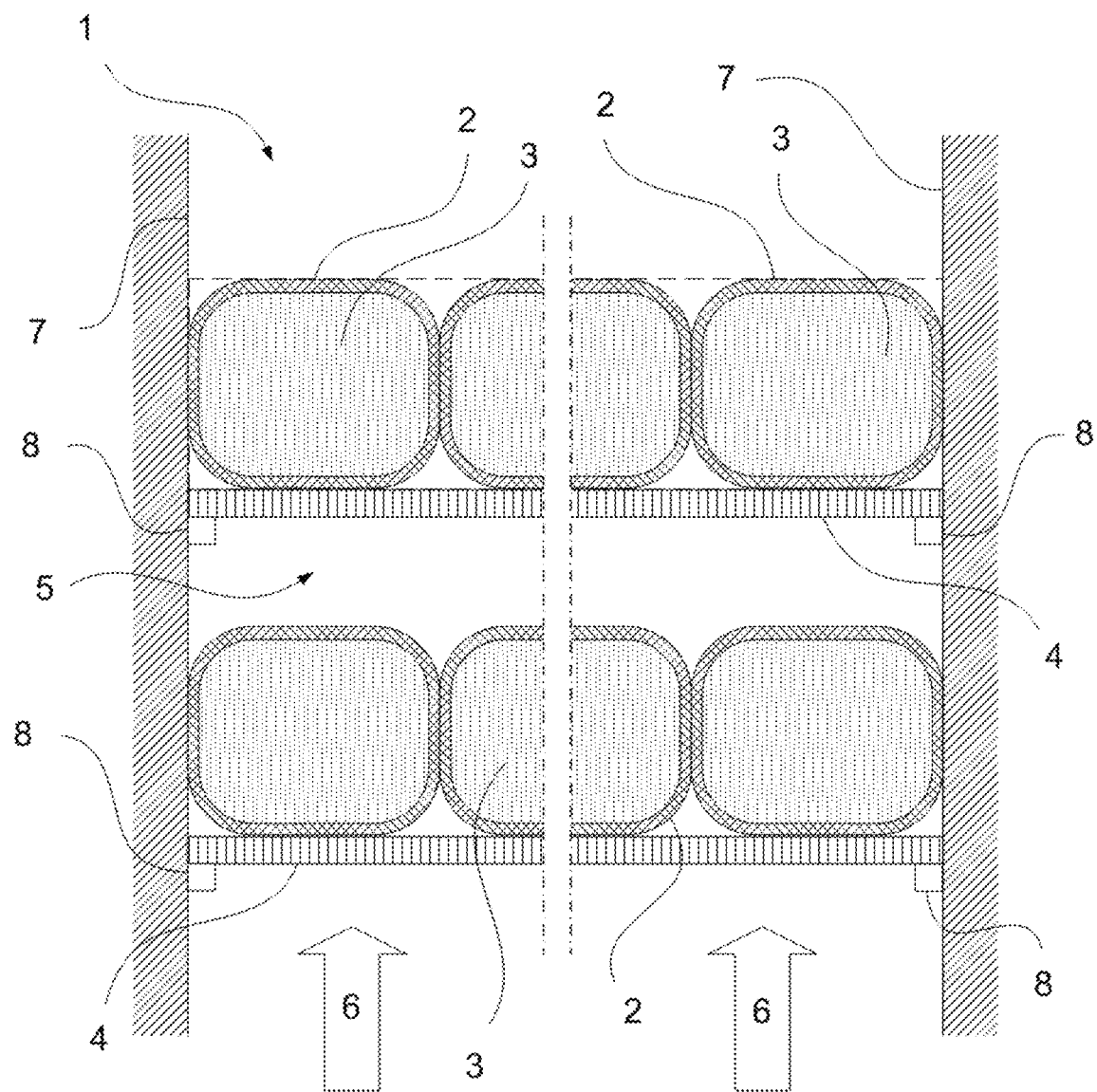
FIG. 1 is a section view of a vertically aligned process gas filter according the invention.

A filter module 1 according to FIG. 1 is arranged to clean a horizontal gas flow 6. The module comprises a plurality of bags 2 containing an active adsorbent 3. The bags are closely arranged side by side between the walls 7 of the filter module 1 on a diffuser 4 such that the gas flow must pass the active adsorbent containing bags. The diffuser comprises a bag carrying sheet with a plurality of passageways for the gas flow. The function of the diffuser is to evenly distribute the gas flow in order to provide a smooth pressure profile and thus a uniform gas flow. The diffuser is placed on brackets 8 on the walls 7 of the filter module.

In the embodiment shown in FIG. 1 there are two layers of active adsorbent bags. Between the two layers of bags there is formed a cavity 5. This cavity helps the gas flow to a uniform passage of the filter module. The gas having passed the first active adsorbent layer will be spread out and building up an even pressure profile towards the next active adsorbent layer. The probability of each gas molecule to reach an active adsorbent particle is thus increased. By the contact with an active adsorbent particle the odour carried by the gas will be adsorbed by the active adsorbent.

Figure 2:
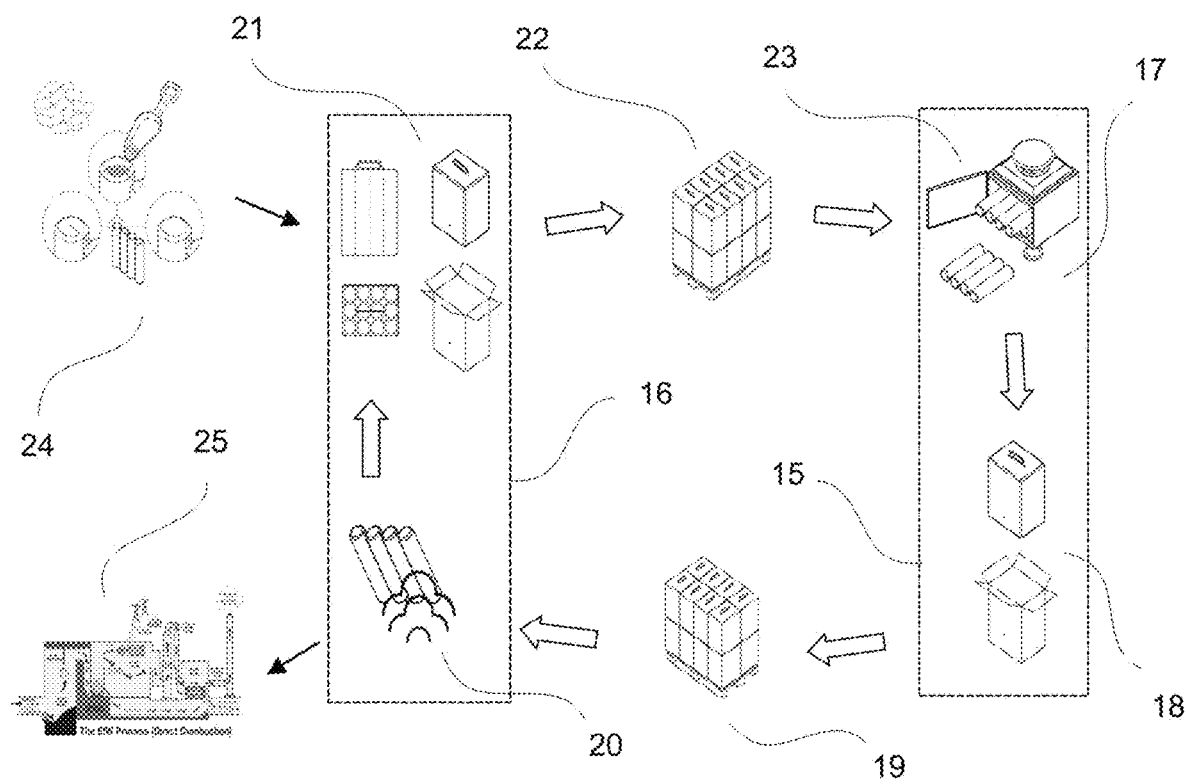
FIG. 2 is a flow chart of a method of recycling saturated active adsorbent in a closed circle according to the invention.

In a recycling process according to FIG. 2 the saturated active adsorbent 3 is sent from an Industrial process plant 15 to a reactivation facility 16. In the embodiment shown the active adsorbent is contained in permeable bags 2. The method comprises a plurality of part processes. All part processes are connected by arrows to show the full circle of the recycling process. In a first process 17 the bags containing saturated active adsorbent are removed from a filter module. In a second process 18 the bags are being packed in a container for transport. In a third process 19 the bag containing container is transported to a reactivation facility 16. In a forth process 20 the saturated active adsorbent is washed and reactivated while still remaining in the bags. In a fifth process 21 the bags are being dried and packed in airtight containers. In a sixth process 22 the airtight containers with the bags are sent back to the Industrial process industry 15. In a seventh process 23 the saturated active adsorbent bags are replaced by reactivated active adsorbent bags in the filter module 1.

Over time a small amount of active adsorbent will be permanently saturated. Thus such permanently saturated adsorbent will not respond to reactivation. When the degree of reusable active adsorbent has fallen beyond an acceptable level the wasted adsorbent bags are sent for combustion 25. As replacement new bags 24 containing fresh activated adsorbent will be introduced into the recycling process.

Although favorable the scope of the invention must not be limited by the embodiments presented but contain also embodiments obvious to a person skilled in the art. For instance any suitable adsorbent may be used. Also any process for reactivating the saturated active adsorbent may be used.

The invention claimed is:

1. A method of recycling saturated adsorbent of a gas filter module of an industrial process plant, the method comprising:
   a first process comprising removing saturated adsorbent contained in heat resistant gas permeable bags from the gas filter module,
   a fourth process comprising washing and reactivating the saturated adsorbent,
   a fifth process comprising drying and packing the reactivated adsorbent In airtight containers, and
   a seventh process comprising replacing the saturated adsorbent by the reactivated adsorbent in the filter module.

2. The method according to claim 1, further comprising:
   a second process comprising packing the saturated adsorbent in a container,
   a third process comprising transporting the packed saturated adsorbent to a reactivation facility, and
   a sixth process comprising transporting the reactivated adsorbent back to the industrial process plant.

3. A system of recycling a saturated adsorbent of a gas filter module in an industrial process plant, the saturated adsorbent being contained in gas permeable heat resistant bags, the system comprising:
   a means for packing the bags containing the saturated adsorbent,
   a transport means for sending the bags containing the saturated adsorbent to a reactivation facility,
   a means for reactivating the saturated adsorbent while still in the bags,
   a means for drying and packing the bags containing the reactivated adsorbent, and
   a transport means for sending the bags containing the reactivated adsorbent back to the industrial process plant.

4. The system according to claim 3, further comprising a means for packing the saturated adsorbent, and a means for replacing the saturated adsorbent with reactivated adsorbent.

* * * * *